US012751908B2

(12) United States Patent
Shinoda et al.

(10) Patent No.: US 12,751,908 B2
(45) Date of Patent: Oct. 6, 2026

(54) PEPTIDE COMPOSITION AND METHOD FOR PRODUCING SAME

(71) Applicant: NITTA GELATIN INC., Osaka (JP)

(72) Inventors: Masaya Shinoda, Yao (JP); Masayuki Mimasu, Yao (JP); Mona Sato, Yao (JP); Toshirou Watanabe, Amagasaki (JP)

(73) Assignee: NITTA GELATIN INC., Osaka (JP)

(*) Notice: Subject to any disclaimer, the term of this patent is extended or adjusted under 35 U.S.C. 154(b) by 698 days.

(21) Appl. No.: 17/917,416

(22) PCT Filed: Mar. 22, 2021

(86) PCT No.: PCT/JP2021/011585
§ 371 (c)(1),
(2) Date: Oct. 6, 2022

(87) PCT Pub. No.: WO2021/205851
PCT Pub. Date: Oct. 14, 2021

(65) Prior Publication Data

US 2023/0149281 A1 May 18, 2023

(30) Foreign Application Priority Data

Apr. 7, 2020 (JP) ................................ 2020-069229

(51) Int. Cl.

| | |
|---|---|
| ***A61K 8/65*** | (2006.01) |
| ***A23L 33/18*** | (2016.01) |
| ***A61K 8/33*** | (2006.01) |
| ***A61K 8/34*** | (2006.01) |
| ***C12N 1/16*** | (2026.01) |

(52) U.S. Cl.
CPC ................ *A61K 8/65* (2013.01); *A23L 33/18* (2016.08); *A61K 8/33* (2013.01); *A61K 8/342* (2013.01); *C12N 1/16* (2013.01)

(58) Field of Classification Search
CPC .. C07K 14/78; C12P 21/06; C12P 7/04; C12P 7/24
See application file for complete search history.

(56) References Cited

U.S. PATENT DOCUMENTS

2004/0241664 A1 12/2004 Dekker et al.

FOREIGN PATENT DOCUMENTS

| | | | | |
|---|---|---|---|---|
| CN | 101294185 A | 10/2008 | | |
| CN | 102199646 A | 9/2011 | | |
| CN | 104105414 A | 10/2014 | | |
| CN | 104856075 A | 8/2015 | | |
| CN | 105255972 A | 1/2016 | | |
| CN | 107365824 A | 11/2017 | | |
| JP | 2003-183129 A | 7/2003 | | |
| JP | 2004-519221 A | 7/2004 | | |
| JP | 2007-84528 A | 4/2007 | | |
| JP | 2007-159557 A | 6/2007 | | |
| JP | 2008-283948 A | 11/2008 | | |
| JP | 2009-112303 A | 5/2009 | | |
| JP | 2012-87091 A | 5/2012 | | |
| JP | 2013-51976 A | 3/2013 | | |
| JP | 2013-236550 A | 11/2013 | | |
| JP | 5686946 B2 * | 3/2015 | .............. | A23L 2/52 |
| JP | 2015-154758 A | 8/2015 | | |
| JP | 2020-127372 A | 8/2020 | | |
| KR | 10-2012-0079964 A | 7/2012 | | |
| KR | 10-1254403 B1 | 4/2013 | | |
| TW | 201919495 A | 6/2019 | | |

OTHER PUBLICATIONS

Taisho (JP5686946B2; machine English translation done on Jul. 28, 2025).*
Zhu (Journal of Agricultural and Food Chemistry; 2015, 63, 7499-7510).*
Communication issued May 7, 2025 in Japanese Application No. 2022-514373.
Chinese Office Action dated Jun. 1, 2023 in Chinese Application No. 202180026984.9.
Hai-Bin et al., "The Optimization of Fermentation of Cod Fish Skin with Aspergillus oryzae to Produce Peptides of LMW and the Research of Bioactivity of Fermentation Peptides", Food and Fermentation Industries, 2011, vol. 37, No. 5, pp. 110-114 (5 pages total).
J.C. Zhu et al., Comparison of Aroma-Active Volatiles in Oolong Tea Infusions Using GC-Olfactometry, GC-FPD, and GC-MS, J. Agric. Food Chem., 2015, vol. 63, pp. 7499-7510.
H. R. Tan et al., Characterisation of key odourants in Japanese green tea using gas chromatography-olfactometry and gas chromatography-mass spectrometry, LWT-Food Science and Technology, Mar. 22, 2019, vol. 108, pp. 221-232.
H. N. Cho et al., Characterization of Off-odor Compounds of Collagen Peptides from Tilapia Scale Using CC-MS-olfactometry, Food Sci. Biotechnol., 2015, vol. 24, No. 2, pp. 403-410.
International Search Report for PCT/JP2021/011585 dated Jun. 8, 2021.
Communication dated May 18, 2026, issued in Indian Application No. 202217058109.

* cited by examiner

*Primary Examiner* — Pancham Bakshi
(74) *Attorney, Agent, or Firm* — Sughrue Mion, PLLC

(57) ABSTRACT

A peptide composition comprises a collagen peptide, and at least three first compounds selected from the group consisting of isovaleric aldehyde, 1-octen-3-ol, phenylacetaldehyde and methional.

4 Claims, No Drawings

PEPTIDE COMPOSITION AND METHOD FOR PRODUCING SAME

This application is a National Stage of International Application No. PCT/JP2021/011585 filed Mar. 22, 2021, claiming priority based on Japanese Patent Application No 2020-069229 filed Apr. 7, 2020.

TECHNICAL FIELD

The present invention relates to a peptide composition and a method for producing the peptide composition.

BACKGROUND ART

Gelatin and collagen peptides obtained by hydrolyzing the gelatin are known to give humans a so-called collagen smell such as a fishy smell or an animal smell because collagen extracted from animals typified by cattle, pigs, sheep, chickens, ostriches and the like or fish is used as a raw material. The collagen smell of the gelatin and collagen peptide (hereinafter, also referred to as "gelatins") may be an obstacle in, for example, applications where being odorless is required. In this connection, Japanese Patent Laying-Open No. 2007-159557 (Patent Literature 1) and Japanese Patent Laying-Open No. 2013-236550 (Patent Literature 2) disclose a technique for reducing the collagen smell.

CITATION LIST

Patent Literature

PTL 1: Japanese Patent Laying-Open No. 2007-159557
PTL 2: Japanese Patent Laying-Open No. 2013-236550

SUMMARY OF INVENTION

Technical Problem

Patent Literature 1 and Patent Literature 2 disclose a technique for reducing a collagen smell by trapping an odor component, which causes a collagen smell, with a specific compound, or chemically reacting the odor component with a specific compound. However, either Patent Literature 1 or Patent Literature 2 does not disclose a technique for reducing the molecular weight of the gelatins. That is, simultaneous realization of reduction of a collagen smell and reduction of the molecular weight of gelatins has not yet been achieved, and development of such a technique is desired.

In view of the circumstances described above, an object of the present invention is to provide a peptide composition having a reduced collagen smell of a collagen peptide obtained by reducing the molecular weight of gelatin or the like, and a method for producing the peptide composition.

Solution to Problem

The present inventors have found that when gelatins are fermented with koji, simultaneous realization of reduction of the molecular weight of the gelatins and reduction of a collagen smell can be achieved, and have completed the present invention.

Specifically, the present invention has characteristics as described below.

[1] The peptide composition according to the present invention comprises a collagen peptide, and at least three first compounds selected from the group consisting of isovaleric aldehyde, 1-octen-3-ol, phenylacetaldehyde and methional.

[2] It is preferable that the peptide composition comprise the four first compounds.

[3] It is preferable that the peptide composition comprise the first compound at 0.05 ppm or more.

[4] It is preferable that the peptide composition comprise the first compound at 0.4 ppm or more.

[5] It is preferable that the collagen peptide have a weight average molecular weight of 20000 or less.

[6] The peptide composition is preferably a food or a cosmetic product.

[7] The method for producing a peptide composition according to the present invention comprises: providing koji containing koji mold, and a collagen raw material; and fermenting the collagen raw material with the koji to obtain a peptide composition.

[8] The bacterial type of the koji mold is preferably a bacterial type belonging to *Aspergillus*.

[9] The bacterial type of the koji is preferably at least one selected from the group consisting of *Aspergillus sojae*, *Aspergillus oryzae* and *Aspergillus luchuensis*.

[10] The collagen raw material is preferably at least any of at least one selected from the group consisting of the following first to sixth groups, collagen extracted from at least one selected from the group, gelatin obtained by treating the collagen, and a gelatin degradation product obtained by hydrolyzing the gelatin:

First group: group consisting of hide, skin, bone, cartilage and tendon of cattle;

Second group: group consisting of hide, skin, bone, cartilage and tendon of pig;

Third group: group consisting of hide, skin, bone, cartilage and tendon of sheep;

Fourth group: group consisting of hide, skin, bone, cartilage and tendon of chicken;

Fifth group: group consisting of hide, skin, bone, cartilage and tendon of ostrich;

Sixth group: group consisting of bone, skin and scale of fish.

[11] The peptide composition according to the present invention comprises a collagen peptide produced by fermenting a collagen raw material with koji.

Advantageous Effects of Invention

According to the above, it is possible to provide a peptide composition having a reduced collagen smell of a collagen peptide obtained by reducing the molecular weight of gelatin or the like, and a method for producing the peptide composition.

DESCRIPTION OF EMBODIMENTS

Hereinafter, embodiments according to the present invention (hereinafter, also referred to as "the present embodiment") will be described in more detail. Here, as used herein, the wording "A to B" means the upper limit and the lower limit of a range (i.e. A or more and B or less), and when a unit is not described for A, but described only for B, the unit for A is identical to the unit for B.

As used herein, the "peptide composition" may be in the form of a solid such as powder, or a liquid such as an aqueous solution obtained by dissolution in water. As used herein, the term "fermentation" means the entirety of a process of generation of a useful organic substance from a raw material by activity of koji mold contained in koji, and is distinguished from "rot" in which an organic substance that is not useful is generated from a raw material by activity of microorganisms.

As used herein, the term "gelatin" may be used when any of a substance name, a gelatin gel and a gelatin solution is mentioned. As in the case of the gelatin, the term "collagen peptide" may be used when any of a substance name and a collagen peptide solution is mentioned.

As used herein, the term "collagen raw material" may be used when at least one "itself" selected from the group consisting of the following first to sixth groups, "collagen" extracted from at least one selected from the group consisting of the following first to sixth groups, "gelatin" obtained by treating the collagen using a known method such as hot water extraction, and a "gelatin degradation product" obtained by hydrolyzing the gelatin are collectively mentioned. Further, the "hydrolysis" of the gelatin includes all of hydrolysis with an acid, hydrolysis with a base, hydrolysis with an enzyme and hydrolysis by heating.

First group: group consisting of hide, skin, bone, cartilage and tendon of cattle Second group: group consisting of hide, skin, bone, cartilage and tendon of pig Third group: group consisting of hide, skin, bone, cartilage and tendon of sheep Fourth group: group consisting of hide, skin, bone, cartilage and tendon of chicken Fifth group: group consisting of hide, skin, bone, cartilage and tendon of ostrich Sixth group: group consisting of bone, skin and scale of fish.

As used herein, the term "collagen smell" means a smell sensed by humans as an unusual smell or an uncomfortable feeling from a fishy smell, an animal smell or the like of the gelatin or gelatin degradation product when the gelatin or gelatin degradation product is obtained from collagen derived from at least one selected from the group consisting of the first to sixth groups. The collagen smell is also sensed by humans as a smell of the collagen peptide when a collagen peptide is obtained from the collagen raw material. In general, oriental people are more sensitive to the collagen smell than western people.

[Peptide Composition]

The peptide composition according to the present embodiment comprises a collagen peptide, and at least three first compounds selected from the group consisting of isovaleric aldehyde, 1-octen-3-ol, phenylacetaldehyde and methional. It is preferable that the peptide composition comprise the four first compounds. Owing to such a characteristic, the present embodiment can provide a peptide composition having a reduced collagen smell of a collagen peptide. In particular, the peptide composition can be obtained by fermenting a collagen raw material with koji.

<Collagen Peptide>

The peptide composition according to the present embodiment comprises a collagen peptide as described above. The collagen peptide is a conventionally known collagen peptide. That is, the collagen peptide means a peptide mixture that may comprise various peptides such as dipeptides, tripeptides, oligopeptides and polypeptides obtained by performing conventionally known treatment on collagen or gelatin. It is preferable that the collagen peptide for the peptide composition be obtained by fermenting a collagen raw material with koji. In this case, the collagen peptide is obtained by reducing the molecular weight of the collagen raw material, and the collagen smell is reduced by masking with a first compound described later.

(Weigh Average Molecular Weight)

It is preferable that the collagen peptide have a weight average molecular weight of 20000 or less. When the weight average molecular weight of the collagen peptide is 20000 or less, the peptide composition can be easily applied to food applications or cosmetic product applications without performing additional treatment. The collagen peptide more preferably has a weight average molecular weight of 10000 or less, still more preferably 6000 or less. The lower limit value of the weight average molecular weight of the collagen peptide is 76. If the weight average molecular weight is above 20000, the collagen peptide may be unsuitable for applications of foods or cosmetic products because the molecular weight is not sufficiently low.

The weight average molecular weight of the collagen peptide contained in the peptide composition can be determined by carrying out size exclusion chromatography (SEC) under the following measurement conditions. The present inventors have confirmed that this measurement method is appropriate even for measurement of a molecular weight exceeding 12000.

Equipment: High performance liquid chromatograph (HPLC) (TOSOH CORPORATION)

Column: TSKGel (registered trademark) G2000 $SW_{XL}$

Column temperature: 40° C.

Eluent: 45 mass % acetonitrile (containing 0.1 mass % TFA)

Flow rate: 1.0 mL/min

Injection amount: 10

Detection: UV 214 nm

Molecular weight marker: The following five types are used.

Cytochrom C Mw: 12000

Aprotinin Mw: 6500

Bacitracin Mw: 1450

Gly-Gly-Tyr-Arg Mw: 451

Gly-Gly-Gly Mw: 189

<First Compound>

The peptide composition according to the present embodiment comprises at least three first compounds selected from the group consisting of isovaleric aldehyde, 1-octen-3-ol, phenylacetaldehyde and methional. The first compound has an action of masking an odor component that causes a collagen smell of the collagen peptide. In the peptide composition, it is considered that the first compound may be produced together with the collagen peptide by fermenting a collagen raw material with koji as described later.

The peptide composition may contain, as the first compound, isovaleric aldehyde, 1-octen-3-ol and phenylacetaldehyde, may contain isovaleric aldehyde, 1-octen-3-ol and methional, may contain isovaleric aldehyde, phenylacetaldehyde and methional, or may contain 1-octen-3-ol, phenylacetaldehyde and methional. It is particularly preferable that the peptide composition contain the four first compounds (isovaleric aldehyde, 1-octen-3-ol, phenylacetaldehyde and methional).

(Isovaleric Aldehyde)

Isovaleric aldehyde is a compound that is also referred to as isovaleric acid aldehyde, 3-methylbutanol or 3-methylbutylaldehyde, and the compound has been conventionally used as a flavor (food additive) or the like.

1-Octen-3-ol

1-Octen-3-ol is a type of unsaturated alcohol, and the compound has been conventionally known to be a component that contributes to the fragrance of matsutake mushroom.

(Phenylacetaldehyde)

Phenylacetaldehyde is a type of aromatic aldehyde, and the compound has been conventionally used as a formulation raw material for fragrances and flavors, etc.

(Methional)

Methional is a type of organosulfur compound, and the compound is also referred to as 3-methylthio-1-propanal. Methional is a compound that has been conventionally known to be contained in soy sauce. Further, methional is known to have an action of weakening the fishy odor of meat and fish.

(Content)

It is preferable that the first compound be contained in the peptide composition at 0.05 ppm or more as a total amount thereof (a total of at least three or four compounds). That is, it is preferable that the peptide composition contain the first compound at 0.05 ppm or more. This enables the peptide composition to have a sufficiently reduced collagen smell.

It is more preferable that the first compound be contained in the peptide composition at 0.4 ppm or more as a total amount thereof. It is more preferable that the peptide composition contain the first compound at 0.4 ppm or more. This enables the peptide composition to have a more sufficiently reduced collagen smell.

It is still more preferable that the first compound be contained in the peptide composition at 0.45 ppm or more as a total amount thereof. This enables more sufficient reduction of the collagen smell. On the other hand, the peptide composition is required to contain the first compound at 0.01 ppm or more as a total amount thereof. If the content of the first compound is less than 0.01 ppm, the masking action on the collagen peptide tends to be insufficient. The upper limit value of the content of the first compound is not particularly limited, and the total amount thereof is preferably 5 ppm or less for preventing the smell of the first compound from adversely affecting the peptide composition.

Qualitative determination and quantitative determination of the first compound contained in the peptide composition can be performed in the following procedure. First, dry powder of the peptide composition is obtained by a production method described later. Further, 0.5 g of the dry powder is dissolved in 4.5 mL of RO water to obtain a measurement sample. Subsequently, the measurement sample is put in gas chromatography mass spectrometers (trade name: "7890 A GC System" manufactured by Agilent Technologies, Inc. and trade name: "JMS-Q1050 GC" manufactured by JEOL Ltd.), vaporized, and then moved into a column of the analyzer with ultrahigh-purity helium as a carrier gas to separate components contained in the measurement sample by compounds. Further, the compound is detected with a detector of the analyzer. Qualitative determination of the first compound can be performed by comparing data obtained from the detector (spectral data) with standard data. Quantitative determination of the first compound can also be performed on the basis of the spectral data (peak area) obtained from the detector.

<Food or Cosmetic Product>

The peptide composition according to the present embodiment is preferably a food or a cosmetic product. When the peptide composition is a food, the peptide composition can be provided as a food having a reduced collagen smell while comprising a collagen peptide. In this case, the peptide composition can impart an additional value of reducing the collagen smell in various applications of foods and beverages comprising a collagen peptide. The peptide composition is particularly useful in, for example, food applications where being odorless is required.

When the peptide composition is a cosmetic product, the peptide composition can be provided as a cosmetic product having a reduced collagen smell while comprising a collagen peptide. In this case, the peptide composition can impart an additional value of, for example, reducing a collagen smell and controlling the amount of a necessary flavor used in various applications of a cosmetic product comprising a collagen peptide. The peptide composition is particularly useful in, for example, cosmetic product applications where being odorless is required.

Here, as used herein, the phrase "when the peptide composition is a food" means a food comprising a collagen peptide, and at least three first compounds selected from the group consisting of isovaleric aldehyde, 1-octen-3-ol, phenylacetaldehyde and methional. The phrase "when the peptide composition is a cosmetic product" means a cosmetic product comprising a collagen peptide, and at least three first compounds selected from the group consisting of isovaleric aldehyde, 1-octen-3-ol, phenylacetaldehyde and methional.

(Food)

When the peptide composition is a food, the peptide composition may be, for example, a food for specified health uses or a food with functional claims. The concentration of the peptide composition in the food for specified health uses or the food with functional claims may be 0.01 to 100 mass %. The concentration of the peptide composition in the food means the concentration of a collagen peptide in the peptide composition because the content of the first compound is very small. Thus, the concentration of the peptide composition in the food can be determined by a conventionally known method for measuring the concentration of a collagen peptide. For example, the concentration of the peptide composition in the food can be determined by measuring the percentage by mass of hydroxyproline in a collagen peptide using a chloramine-T method. It is also possible to determine the concentration of the peptide composition in the food by measuring the percentage by mass of hydroxyproline in a collagen peptide using an amino acid analyzer.

(Cosmetic Product)

When the peptide composition is a cosmetic product, the concentration of the peptide composition in the cosmetic product may be 0.01 to 100 mass %. As in the case of the food, the concentration of the peptide composition in the cosmetic product means the concentration of a collagen peptide in the peptide composition because the content of the first compound is very small. Thus, the concentration of the peptide composition contained in the cosmetic product can be determined by a method identical to the above-mentioned method for measuring the concentration of the peptide composition in the food.

[Method for Producing Peptide Composition]

The method for producing a peptide composition according to the present embodiment comprises providing koji containing koji mold and a collagen raw material (first step), and fermenting the collagen raw material with the koji to obtain a peptide composition (second step). The method for producing a peptide composition, which has such a characteristic, enables production of a peptide composition having a collagen peptide with a reduced molecular weight and having a reduced collagen smell of the collagen peptide.

The reason why in the peptide composition produced by the above-described production method, a collagen peptide with a reduced molecular weight can be obtained and the collagen smell can be reduced is not known in detail, but may be explained by the following mechanism. That is, the production method comprises fermenting a collagen raw material with koji to obtain a peptide composition (second step). The koji is known to comprise a variety of enzymes produced by proliferation of koji mold. Thus, in the second step, such a variety of enzymes may exert their action to decompose or oxidize and reduce polypeptides in the collagen raw material and saccharides in the koji. Therefore, in the second step, it is considered that a variety of enzymes act to reduce the molecular weight of the polypeptide and produce the first compound that masks an odor component causing the collagen smell. Accordingly, it is considered that the above-described production method may enable production of a peptide composition having a collagen peptide with a reduced molecular weight and having a reduced collagen smell of the collagen peptide. Hereinafter, the steps in the method for producing a peptide composition according to the present embodiment will be described.

<First Step>

The first step is a step of providing koji containing koji mold, and a collagen raw material. The first step is carried out for the purpose of providing the materials (koji containing koji mold and a collagen raw material) required for producing the peptide composition.

(Collagen Raw Material)

The collagen raw material may be at least any of at least one "itself" selected from the group consisting of the following first to sixth groups, "collagen" extracted from at least one selected from the group consisting of the following first to sixth groups, "gelatin" obtained by treating the collagen using a known method such as hot water extraction, and a "gelatin degradation product" obtained by hydrolyzing the gelatin as described above.

First group: group consisting of hide, skin, bone, cartilage and tendon of cattle Second group: group consisting of hide, skin, bone, cartilage and tendon of pig Third group: group consisting of hide, skin, bone, cartilage and tendon of sheep Fourth group: group consisting of hide, skin, bone, cartilage and tendon of chicken Fifth group: group consisting of hide, skin, bone, cartilage and tendon of ostrich Sixth group: group consisting of bone, skin and scale of fish.

That is, in the first step, it is preferable that at least one selected from the group consisting of at least one selected from the group consisting of the first to sixth groups, the collagen, the gelatin, and the gelatin degradation product be provided as the collagen raw material. In the first step, one collagen raw material selected from these may be provided, or two or more collagen raw materials may be provided in combination. The group consisting of the first to sixth groups, the collagen, the gelatin and the gelatin degradation product can be all provided by conventionally known methods.

Here, it is preferable that the gelatin be obtained by performing pretreatment by acid treatment or alkali treatment, hot water extraction, purification treatment and sterilization treatment in this order on collagen extracted from at least one selected from the group consisting of the first to sixth groups. This enables provision of gelatin having high safety for the human body etc., and therefore a peptide composition to be produced in the present embodiment can be applied to the applications of the above-described food or cosmetic product. Further, such gelatin is also excellent in economic performance. The pretreatment by acid treatment or alkali treatment, the hot water extraction, the purification treatment and the sterilization treatment can be all performed by conventionally known methods.

The gelatin degradation product can be obtained by subjecting the gelatin to any of hydrolysis with an acid, hydrolysis with a base, hydrolysis with an enzyme and hydrolysis by heating, each of which has been conventionally known. The weight average molecular weight of the gelatin degradation product should not be particularly limited, and is preferably 20000 or less, more preferably 10000 or less, for example. The lower limit value of the weight average molecular weight of the gelatin degradation product is 76. The weight average molecular weight of the gelatin degradation product can be determined by a measurement method identical to that described above for the weight average molecular weight of a collagen peptide.

(Koji Containing Koji Mold)

Koji containing koji mold can be provided by a heretofore known method as long as koji that allows the effects of the present embodiment to be obtained by carrying out the second step described later is selected. That is, koji mold as seed koji is inoculated in rice, barley, wheat or a cereal such as soybeans, and then proliferated in the rice, the barley, the wheat or the cereal to obtain the koji. It is preferable that the koji mold be inoculated at 0.01 to 1 mass % with respect to the rice, the barley, the wheat or the cereal. As used herein, the category of "cereal" includes all of bran, wheat bran, soybean curd lees and defatted soybeans in addition to the above-described soybeans. In provision of koji containing koji mold, it is preferable that a koji chamber for preventing contamination of other bacteria be provided to create an environment which facilitates proliferation of koji mold, and necessary operations be carried out in the koji chamber.

The bacterial type of the koji mold is preferably a bacterial type belonging to *Aspergillus*. The bacterial type of the koji mold is more preferably at least one selected from the group consisting of *Aspergillus sojae, Aspergillus oryzae* and *Aspergillus luchuensis*. Since these bacterial types have been confirmed to be safe for the human body etc., the peptide composition produced in the present embodiment can be easily applied to the applications of the above-described food or cosmetic product. In the first step, koji containing one selected from the group of these bacterial types may be provided, or koji containing two or more selected from the group of the bacterial types may be provided.

<Second Step>

The second step is a step of fermenting the collagen raw material with the koji to obtain a peptide composition. The second step is carried out for the purpose of reducing the molecular weight of the collagen raw material to obtain a collagen peptide, and reducing a collagen smell of the collagen peptide. In the second step, for example, the collagen raw material and the koji are put in warm water, and cultured in the warm water for a predetermined time to ferment the collagen raw material with the koji, so that it is possible to obtain a fermented product comprising the peptide composition.

Specifically, it is preferable that from the collagen raw material at 0.1 to 75 mass %, the koji at 0.1 to 20 mass % in terms of dry mass (dry weight) and water at 5 to 99.8 mass %, a dispersion liquid containing these components at 100 mass % in total be prepared, and the dispersion liquid be adjusted to a pH of 2 to 10, and then cultured for 1 to 24 hours while the dispersion liquid is maintained at a temperature of 10 to 65° C. In this way, a fermented product comprising the peptide composition comprising a collagen peptide, and at least three first compounds selected from the group consisting of isovaleric aldehyde, 1-octen-3-ol, phenylacetaldehyde and methional can be obtained.

It is also preferable to obtain the fermented product by the following method. That is, first, from the koji at 0.1 to 40 mass % in terms of dry mass (dry weight) and water at 60 to 99.9 mass %, a dispersion liquid containing these components at 100 mass % in total is prepared, and cultured for 1 to 24 hours while the dispersion liquid is maintained at a temperature of 10 to 65° C. The dispersion liquid is coarsely filtered with a nylon mesh, and filtered with diatomaceous earth and cellulose to obtain a koji extraction liquid. Next, from the collagen raw material at 0.1 to 75 mass % and the koji extraction liquid at 0.1 to 99.9 mass %, a dispersion liquid containing these components at 100 mass % in total is prepared, and the dispersion liquid is adjusted to a pH of 2 to 10, and then cultured for 1 to 24 hours while the dispersion liquid is maintained at a temperature of 10 to 65° C. A fermented product containing a peptide composition can also be obtained by this method. When a fermented product is obtained by applying this method, a peptide composition can be obtained without carrying out a separation treatment step described later on the fermented product. However, carrying out at least any of a purification step and a deodorization step described later on the fermented product is not excluded.

The temperature of the warm water during culture is preferably 15 to 60° C., more preferably 20 to 50° C. If the temperature of warm water during culture is below 10° C. or above 65° C., reduction of the molecular weight of the collagen raw material, reduction of the collagen smell and the like may be insufficient due to a decrease in efficiency of fermentation with koji.

Further, the culture time is preferably 2 to 18 hours, more preferably 4 to 8 hours. If the culture time exceeds 24 hours, economic efficiency may be compromised. If the culture time is below 1 hour, fermentation with koji may be insufficient.

The content of the collagen raw material in the warm water during culture is preferably 10 to 45 mass %, more preferably 20 to 40 mass %. If the content of the collagen raw material in the warm water during culture is less than 0.1 mass %, economic efficiency may be compromised. If the content of the collagen raw material in the warm water during culture is above 75 mass %, working efficiency may be compromised.

The content of koji in the dispersion liquid composed of the koji, the collagen raw material and water is preferably 1 to 15 mass %, more preferably 5 to 10 mass %, in terms of dry mass (dry weight). If the content of koji in the warm water during culture is less than 0.1 mass % in terms of dry mass (dry weight), fermentation by koji may be insufficient. If the content of koji in the warm water during culture is above 20 mass % in terms of dry mass (dry weight), economic efficiency may be compromised. The content of koji in the koji extraction liquid is preferably 2 to 25 mass %, more preferably 8 to 16 mass %. If the content of koji is less than 0.1 mass % in terms of dry mass (dry weight) in the koji extraction liquid, fermentation by koji may be insufficient. If the content of koji in the koji extraction liquid is above 40 mass % in terms of dry mass (dry weight), economic efficiency may be compromised.

The value of pH during culture of the dispersion liquid is preferably 2 to 10, more preferably 5 to 8. If the value of pH during culture of the dispersion liquid is lower than 2 or higher than 10, reduction of the molecular weight of the collagen raw material, reduction of the collagen smell and the like may be insufficient.

Here, in the second step, after the fermented product comprising a peptide composition is obtained through the above-described step, the temperature thereof is set to 75° C. or higher depending on the purpose to inactivate the action (activity) of koji mold, so that progression of fermentation of the collagen raw material by koji can be stopped. Specifically, the weight average molecular weight of the collagen peptide in the fermented product may be measured, and confirmed to be smaller than the molecular average molecular weight of the collagen raw material, or when the culture time reaches a predetermined time, for example 24 hours, the temperature of the fermented product may be set to 75° C. or higher to stop progression of fermentation of the collagen raw material by koji. The weight average molecular weight of the collagen peptide in the fermented product can be determined by a measurement method identical to that described above for the weight average molecular weight of a collagen peptide.

(Other Steps)

It is preferable that the second step include a separation treatment step for separating and obtaining a peptide composition from the fermented product. For the separation treatment step, conventionally known separation treatment can be applied. A peptide composition can be separated from the fermented product by separation treatment such as coarse filtration with a nylon mesh, centrifugation or paper filtration with commercially available filter paper. In this way, a peptide composition comprising a collagen peptide and at least three first compounds selected from the group consisting of isovaleric aldehyde, 1-octen-3-ol, phenylacetaldehyde and methional can be obtained.

Further, it is also preferable that the second step include a step of subjecting the peptide composition obtained by applying the separation treatment step or the fermented product to purification treatment for the purpose of enhancing its transparency or the like (purification step). In this purification step, conventionally known purification treatment can be applied, and for example, purification treatment with diatomaceous earth or purification treatment by precision filtration can be performed. Further performing deodorization treatment (deodorization step) by using activated carbon or the like, if necessary, is not excluded.

The peptide composition obtained as described above can be stored as such in the form of a solution. Further, peptide composition dry powder can be obtained by applying a conventionally known method such as spray drying or drum drying to the peptide composition in the form of a solution, and stored as such.

Effect

From the above, the method for producing a peptide composition according to the present embodiment enables production of a peptide composition comprising a collagen peptide, and at least three first compounds selected from the group consisting of isovaleric aldehyde, 1-octen-3-ol, phenylacetaldehyde and methional.

EXAMPLES

Hereinafter, the present invention will be described in more detail by way of Examples, which should not be construed as limiting the present invention. In the following description, samples 1 to 11 and sample 12 are peptide compositions of Examples, and samples 101 to 103 are peptide compositions of Comparative Examples.

[Preparation of Sample]

<Sample 1>

(First Step)

Koji containing koji mold and a collagen raw material were provided in the following procedure.

<Provision of Koji Containing Koji Mold>

Barley bran koji obtained by inoculating *Aspergillus sojae* (manufactured by Higuchi Matsunosuke Shoten Co., Ltd.) was provided as koji containing koji mold.

<Provision of Collagen Raw Material>

A Tilapia scale-derived gelatin degradation product having a weight average molecular weight of about 4000 (trade name: "HDL-50 SP" manufactured by Nitta Gelatin Inc.) was provided as a collagen raw material.

(Second Step)

A peptide composition was obtained by fermenting the collagen raw material with the koji in the following procedure. First, a dispersion liquid composed of 40 mass % of the collagen raw material, 8 mass % (dry weight) of the barley bran koji and 52 mass % of RO water was prepared, and cultured for 6 hours while the dispersion liquid was maintained at a temperature of 40° C. Thereafter, the temperature of the dispersion liquid was set to 75° C., and the dispersion liquid was maintained at a temperature of about 75° C. for 60 minutes to inactivate koji mold in the barley bran koji, so that a fermented product comprising a peptide composition was obtained.

Subsequently, the fermented product was centrifuged at a centrifugal acceleration of 1610 G for 30 minutes, and the supernatant thereof was taken to obtain a peptide composition of sample 1.

The peptide composition of sample 1 was an aqueous solution, and the weight average molecular weight thereof was measured, and confirmed to be smaller than the weight average molecular weight of the collagen raw material. By analysis using the gas chromatography mass spectrometer, the peptide composition of sample 1 was confirmed to contain isovaleric aldehyde, 1-octen-3-ol, phenylacetaldehyde and methional as the first compound.

<Sample 2>

A peptide composition of sample 2 was obtained in the same manner as in preparation of sample 1 except that barley bran koji obtained by inoculating *Aspergillus oryzae* (manufactured by Higuchi Matsunosuke Shoten Co., Ltd.) was provided as koji containing koji mold.

The peptide composition of sample 2 was an aqueous solution, and the weight average molecular weight thereof was measured, and confirmed to be smaller than the weight average molecular weight of the collagen raw material. By analysis using the gas chromatography mass spectrometer, the peptide composition of sample 2 was confirmed to contain isovaleric aldehyde, 1-octen-3-ol, phenylacetaldehyde and methional as the first compound.

<Sample 3>

A peptide composition of sample 3 was obtained in the same manner as in preparation of sample 1 except that barley bran koji obtained by inoculating *Aspergillus luchuensis* (manufactured by Higuchi Matsunosuke Shoten Co., Ltd.) was provided as koji containing koji mold.

The peptide composition of sample 3 was an aqueous solution, and the weight average molecular weight thereof was measured, and confirmed to be smaller than the weight average molecular weight of the collagen raw material. By analysis using the gas chromatography mass spectrometer, the peptide composition of sample 3 was confirmed to contain isovaleric aldehyde, 1-octen-3-ol, phenylacetaldehyde and methional as the first compound.

<Sample 4>

A peptide composition of sample 4 was obtained in the same manner as in preparation of sample 1 except that pig hide-derived gelatin (trade name: "BCN-HL" manufactured by Nitta Gelatin Inc., weight average molecular weight: about 65000) was provided as a collagen raw material.

The peptide composition of sample 4 was an aqueous solution, and the weight average molecular weight thereof was measured, and confirmed to be smaller than the weight average molecular weight of the collagen raw material. By analysis using the gas chromatography mass spectrometer, the peptide composition of sample 4 was confirmed to contain isovaleric aldehyde, 1-octen-3-ol, phenylacetaldehyde and methional as the first compound.

<Sample 5>

A peptide composition of sample 5 was obtained in the same manner as in preparation of sample 2 except that pig hide-derived gelatin (trade name: "BCN-HL" manufactured by Nitta Gelatin Inc., weight average molecular weight: about 65000) was provided as a collagen raw material.

The peptide composition of sample 5 was an aqueous solution, and the weight average molecular weight thereof was measured, and confirmed to be smaller than the weight average molecular weight of the collagen raw material. By analysis using the gas chromatography mass spectrometer, the peptide composition of sample 5 was confirmed to contain isovaleric aldehyde, 1-octen-3-ol, phenylacetaldehyde and methional as the first compound.

<Sample 6>

A peptide composition of sample 6 was obtained in the same manner as in preparation of sample 3 except that pig hide-derived gelatin (trade name: "BCN-HL" manufactured by Nitta Gelatin Inc., weight average molecular weight: about 65000) was provided as a collagen raw material.

The peptide composition of sample 6 was an aqueous solution, and the weight average molecular weight thereof was measured, and confirmed to be smaller than the weight average molecular weight of the collagen raw material. By analysis using the gas chromatography mass spectrometer, the peptide composition of sample 6 was confirmed to contain isovaleric aldehyde, 1-octen-3-ol, phenylacetaldehyde and methional as the first compound.

<Sample 7>

(First Step)

Koji containing koji mold and a collagen raw material were provided in the following procedure.

<Provision of Koji Containing Koji Mold>

Barley bran koji obtained by inoculating *Aspergillus sojae* (manufactured by Higuchi Matsunosuke Shoten Co., Ltd.) was provided as koji containing koji mold.

<Provision of Collagen Raw Material>

Cattle bone-derived gelatin (trade name: "#250" manufactured by Nitta Gelatin Inc., weight average molecular weight: about 190000) was provided as a collagen raw material.

(Second Step)

A peptide composition was obtained by fermenting the collagen raw material with the koji in the following procedure. First, a dispersion liquid composed of the collagen raw material at 10 mass %, the barley bran koji at 2 mass % (dry weight) and RO water at 88 mass % was prepared, and cultured for 6 hours while the dispersion liquid was maintained at a temperature of 40° C. Thereafter, the temperature of the dispersion liquid was set to 75° C., and the dispersion liquid was maintained at a temperature of about 75° C. for 60 minutes to deactivate koji mold in the barley bran koji, so that a fermented product containing a peptide composition was obtained.

Subsequently, the fermented product was centrifuged at a centrifugal acceleration of 1610 G for 30 minutes, and the supernatant thereof was taken to obtain a peptide composition of sample 7.

The peptide composition of sample 7 was an aqueous solution, and the weight average molecular weight thereof was measured, and confirmed to be smaller than the weight average molecular weight of the collagen raw material. By analysis using the gas chromatography mass spectrometer, the peptide composition of sample 7 was confirmed to contain isovaleric aldehyde, 1-octen-3-ol, phenylacetaldehyde and methional as the first compound.

<Sample 8>

A peptide composition of sample 8 was obtained in the same manner as in preparation of sample 7 except that pig hide-derived gelatin (trade name: "BCN-HL" manufactured by Nitta Gelatin Inc., weight average molecular weight: about 65000) was provided as a collagen raw material.

The peptide composition of sample 8 was an aqueous solution, and the weight average molecular weight thereof was measured, and confirmed to be smaller than the weight average molecular weight of the collagen raw material. By analysis using the gas chromatography mass spectrometer, the peptide composition of sample 8 was confirmed to contain isovaleric aldehyde, 1-octen-3-ol, phenylacetaldehyde and methional as the first compound.

<Sample 9>

A peptide composition of sample 9 was obtained in the same manner as in preparation of sample 7 except that Tilapia scale-derived gelatin (manufactured by Nitta Gelatin Inc., weight average molecular weight: about 150000) was provided as a collagen raw material.

The peptide composition of sample 9 was an aqueous solution, and the weight average molecular weight thereof was measured, and confirmed to be smaller than the weight average molecular weight of the collagen raw material. By analysis using the gas chromatography mass spectrometer, the peptide composition of sample 9 was confirmed to contain isovaleric aldehyde, 1-octen-3-ol, phenylacetaldehyde and methional as the first compound.

<Sample 10>

A peptide composition of sample 10 was obtained in the same manner as in preparation of sample 4 except that in the second step, centrifugation was performed to obtain a supernatant, the supernatant was then subjected to filtration with filter paper and filtration with diatomaceous earth, and the peptide composition was formed into dry powder by using a spray dryer (manufactured by Ookawara Manufacturing Co., Ltd.).

The peptide composition of sample 10 was dry powder, and the weight average molecular weight thereof was measured, and confirmed to be smaller than the weight average molecular weight of the collagen raw material. By analysis using the gas chromatography mass spectrometer, the peptide composition of sample 10 was confirmed to contain isovaleric aldehyde, phenylacetaldehyde and methional as the first compound.

<Sample 11>

(First Step)

Koji containing koji mold, and a collagen raw material were provided in the following procedure.

<Provision of Koji Containing Koji Mold>

Barley bran koji obtained by inoculating *Aspergillus sojae* (manufactured by Higuchi Matsunosuke Shoten Co., Ltd.) was provided as koji containing koji mold.

<Provision of Collagen Raw Material>

Dehaired cattle hide (made in U.S.) was washed with water in running water, and then mechanically finely divided by using a commercially available meat chopper with a plate having pores having a diameter of 6 mm and a stone mill-type ultra-fine grinder (manufactured by Masuko Sangyo Co., Ltd.), so that paste-like cattle hide collagen was obtained. In this way, a collagen raw material was provided. The weight average molecular weight of the collagen raw material is difficult to accurately calculate, and may be 300000 or more.

(Second Step)

A peptide composition was obtained by fermenting the collagen raw material with the koji in the following procedure. First, a dispersion liquid composed of the collagen raw material (cattle hide collagen) at 2.5 mass %, the barley bran koji at 0.5 mass % (dry weight) and RO water at 97 mass % was prepared, and cultured for 24 hours while the dispersion liquid was maintained at a temperature of 40° C. Thereafter, the temperature of the dispersion liquid was set to 75° C., and the dispersion liquid was maintained at a temperature of about 75° C. for 60 minutes to deactivate koji mold in the barley bran koji, so that a fermented product comprising a peptide composition was obtained. This fermented product was taken as a peptide composition of sample 11.

The peptide composition of sample 11 was a dispersion liquid (suspension liquid), and the weight average molecular weight thereof was measured, and confirmed to be smaller than the weight average molecular weight of the collagen raw material. By analysis using the gas chromatography mass spectrometer, the peptide composition of sample 11 was confirmed to contain isovaleric aldehyde, 1-octen-3-ol, phenylacetaldehyde and methional as the first compound.

<Sample 12>

(First Step)

Koji containing koji mold, and a collagen raw material were provided in the following procedure.

<Provision of Koji Containing Koji Mold>

Barley bran koji obtained by inoculating *Aspergillus sojae* (manufactured by Higuchi Matsunosuke Shoten Co., Ltd.) was provided as koji containing koji mold.

<Provision of Collagen Raw Material>

Pig hide-derived gelatin (trade name: "BCN-HL" manufactured by Nitta Gelatin Inc., weight average molecular weight: about 65000) was provided as a collagen raw material.

(Second Step)

A peptide composition was obtained by fermenting the collagen raw material with the koji in the following procedure. First, a dispersion liquid composed of the barely bran koji at 6 mass % (dry weight) and RO water at 94 mass % was prepared, and stirred for 1 hour while the dispersion liquid was maintained at a temperature of 40° C. Thereafter, the dispersion liquid was coarsely filtered with a nylon mesh and filtered with diatomaceous earth and cellulose to obtain a koji extraction liquid. Subsequently, a dispersion liquid composed of the collagen raw material at 40 mass % and the koji extraction liquid at 60 mass % was prepared, and cultured for 6 hours while the dispersion liquid was maintained at a temperature of 40° C. Thereafter, the temperature of the dispersion liquid was set to 60° C., the dispersion liquid was maintained at a temperature of about 60° C. for 60 minutes to perform low-temperature sterilization, and formed into dry powder by using a spray dryer (manufactured by Ookawara Manufacturing Co., Ltd.), so that a peptide composition of sample 12 was obtained.

The peptide composition of sample 12 was dry powder, and the weight average molecular weight thereof was measured, and confirmed to be smaller than the weight average molecular weight of the collagen raw material. By analysis using the gas chromatography mass spectrometer, the peptide composition of sample 12 was confirmed to contain isovaleric aldehyde, 1-octen-3-ol, phenylacetaldehyde and methional as the first compound.

<Sample 101>

A dispersion liquid composed of Tilapia scale-derived gelatin having a weight average molecular weight of about 150000 (manufactured by Nitta Gelatin Inc.) at 40 mass %, Alcalase 2.4 LFG (manufactured by Novozymes Japan Ltd.) as a *Bacillus Licheniformis*-derived enzyme at 0.4 mass %, and RO water at 59.6 mass % was prepared. Subsequently, the dispersion liquid was cultured for 2 hours while the dispersion liquid was maintained at a temperature of 60° C. Thereafter, the temperature of the dispersion liquid was set to 75° C., the dispersion liquid was maintained at a temperature of about 75° C. for 60 minutes to deactivate the enzyme, and a deodorization step using activated carbon was carried out to obtain a peptide composition of sample 101.

[First Test]

<Sensory Odor Test>

Samples 1 to 6 and samples 101 to 103 were each adjusted to a collagen peptide concentration of 10 mass % using RO water, and provided in an amount of 20 mL. Further, for sample 10, a solution (20 mL) obtained by dissolving 2 g of the dry powder in 18 mL of RO water was provided. For the samples, five evaluators conducted a sensory odor test on how strongly the collagen smell was sensed. In the sensory odor test, scores 1 to 4 were given to the samples as shown in Table 1. As the score increases, the so-called collagen smell such as a fishy smell or an animal smell is evaluated to be reduced. Table 2 shows the results.

TABLE 1

| Score | Evaluation |
|---|---|
| 1 | Very strong collagen smell |
| 2 | Strong collagen smell |
| 3 | Slight collagen smell |
| 4 | Little collagen smell |

TABLE 2

| | Evaluator A | Evaluator B | Evaluator C | Evaluator D | Evaluator E | Average value |
|---|---|---|---|---|---|---|
| Sample 1 | 3 | 4 | 4 | 4 | 4 | 3.8 |
| Sample 2 | 4 | 3 | 4 | 4 | 3 | 3.6 |
| Sample 3 | 4 | 2 | 4 | 4 | 4 | 3.6 |
| Sample 4 | 3 | 4 | 4 | 4 | 4 | 3.8 |
| Sample 5 | 4 | 3 | 4 | 4 | 3 | 3.6 |
| Sample 6 | 4 | 2 | 3 | 4 | 2 | 3 |
| Sample 10 | 3 | 4 | 4 | 4 | 3 | 3.6 |
| Sample 101 | 1 | 2 | 2 | 3 | 2 | 2 |
| Sample 102 | 1 | 1 | 1 | 1 | 1 | 1 |
| Sample 103 | 1 | 1 | 1 | 2 | 1 | 1.2 |

<Sample 102>

A dispersion liquid composed of pig hide-derived gelatin having a weight average molecular weight of about 65000 (trade name: "BCN-HL" manufactured by Nitta Gelatin Inc.) at 40 mass %, Papain W-40 (manufactured by Amano Enzyme Inc.) as a papaya-derived enzyme at 0.4 mass %, and RO water at 59.6 mass % was prepared, and cultured for 2 hours while the dispersion liquid was maintained at a temperature of 60° C. Thereafter, the temperature of the dispersion liquid was set to 75° C., and the dispersion liquid was maintained at a temperature of about 75° C. for 60 minutes to deactivate the enzyme, so that a peptide composition of sample 102 was obtained.

<Sample 103>

A dispersion liquid composed of pig hide-derived gelatin having a weight average molecular weight of about 65000 (trade name: "BCN-HL" manufactured by Nitta Gelatin Inc.) at 10 mass %, Flavourzyme (manufactured by Novozymes Japan Ltd.) as an *Aspergillus oryzae*-derived enzyme at 0.5 mass %, and RO water at 89.5 mass % was prepared, and cultured for 6 hours while the dispersion liquid was maintained at a temperature of 55° C. Thereafter, the temperature of the dispersion liquid was set to 75° C., and the dispersion liquid was maintained at a temperature of about 75° C. for 60 minutes to deactivate the enzyme, so that a peptide composition of sample 103 was obtained.

<Discussion>

From Table 2, the peptide compositions of samples 1 to 6 and 10 are evaluated to have a reduced collagen smell as compared to the peptide compositions of samples 101 to 103.

[Second Test]

<Qualitative and Quantitative Tests>

Solutions with samples 4, 5 and 102 adjusted to a collagen peptide concentration of 10 mass % were each provided in an amount of 5 mL. Further, for sample 10, a solution (5 mL) obtained by dissolving 0.5 g of the dry powder in 4.5 mL of RO water was provided. For each of the samples, components in the sample were identified with gas chromatography mass spectrometers (trade name: "7890 A GC System" manufactured by Agilent Technologies, Inc. and trade name: "JMS-Q1050 GC" manufactured by JEOL Ltd.) to conduct qualitative and quantitative tests on the first compound in the sample. The methods for the qualitative and quantitative tests were as described above. Table 3 shows the results. The unit of the values shown in Table 3 is ppm, and "N.D." indicates that the relevant compound was not detected.

TABLE 3

| | Isovaleric aldehyde | 1-Octen-3-ol | Phenylacetaldehyde | Methional |
|---|---|---|---|---|
| Sample 102 | N.D | N.D | N.D | 0.04 |
| Sample 4 | 0.27 | 0.06 | 0.10 | 0.05 |
| Sample 5 | 0.30 | 0.05 | 0.08 | 0.04 |
| Sample 10 | 0.60 | N.D | 0.32 | 0.30 |

<Discussion>

Table 3 reveals that the peptide compositions of samples 4, 5 and 10 all had at least three first compounds selected from the group consisting of isovaleric aldehyde, 1-octen-3-ol, phenylacetaldehyde and methional. On the other hand, the peptide composition of sample 102 had only methional.

[Third Test]

<Weight Average Molecular Weight of Collagen Peptide>

For samples 1 to 3, the degree to which the molecular weight of the collagen raw material had been reduced to form the collagen peptide by passing through the second step was examined. Specifically, for samples 1 to 3, the weight average molecular weight of the collagen peptide contained in the peptide composition after fermentation for 6 hours in the second step was determined by the above-described measurement method. Table 4 shows the results.

TABLE 4

| | Weight average molecular weight after fermentation for 6 hours (Mw) |
|---|---|
| Sample 1 | 944 |
| Sample 2 | 970 |
| Sample 3 | 2924 |

<Discussion>

From Table 4, it is understood that for the peptide compositions of samples 1 to 3, the molecular weight of the collagen raw material was reduced by passing through the second step.

[Fourth Test]

<Weight Average Molecular Weight of Collagen Peptide>

For samples 4 to 6, the degree to which the molecular weight of the collagen raw material had been reduced to form the collagen peptide by passing through the second step was examined. Specifically, for samples 4 to 6, the weight average molecular weight of the collagen peptide contained in the peptide composition after fermentation for 6 hours in the second step was determined by the above-described measurement method. Table 5 shows the results.

TABLE 5

| | Weight average molecular weight after fermentation for 6 hours (Mw) |
|---|---|
| Sample 4 | 1164 |
| Sample 5 | 1318 |
| Sample 6 | 5658 |

<Discussion>

From Table 5, it is understood that for the peptide compositions of samples 4 to 6, the molecular weight of the collagen raw material was reduced by passing through the second step.

[Fifth Test]

<Weight Average Molecular Weight of Collagen Peptide>

For samples 7 to 9, the degree to which the molecular weight of the collagen raw material had been reduced to form the collagen peptide by passing through the second step was examined. Specifically, for samples 7 to 9, the weight average molecular weight of the collagen peptide contained in the peptide composition after fermentation for 6 hours in the second step was determined by the above-described measurement method. Table 6 shows the results.

TABLE 6

| | Weight average molecular weight after fermentation for 6 hours (Mw) |
|---|---|
| Sample 7 | 730 |
| Sample 8 | 710 |
| Sample 9 | 680 |

<Discussion>

From Table 6, it is understood that for the peptide compositions of samples 7 to 9, the molecular weight of the collagen raw material was reduced by passing through the second step.

[Sixth Test]

<Weight Average Molecular Weight of Collagen Peptide>

For sample 10, the degree to which the molecular weight of the collagen raw material had been reduced to form the collagen peptide by passing through the second step was examined. Specifically, for sample 10, the weight average molecular weight of the collagen peptide contained in the peptide composition after fermentation for 6 hours in the second step was determined by the above-described measurement method. Table 7 shows the results.

TABLE 7

| | Weight average molecular weight after fermentation for 6 hours (Mw) |
|---|---|
| Sample 10 | 1102 |

<Discussion>

From Table 7, it is understood that for the peptide composition of sample 10, the molecular weight of the collagen raw material was reduced by passing through the second step.

[Seventh Test]

<Weight Average Molecular Weight of Collagen Peptide>

For sample 11, the degree to which the molecular weight of the collagen raw material had been reduced to form the collagen peptide by passing through the second step was examined. Specifically, for sample 11, the weight average molecular weight of the collagen peptide contained in the peptide composition after fermentation for 24 hours in the second step was determined by the above-described measurement method. Table 8 shows the results.

TABLE 8

| | Weight average molecular weight after fermentation for 24 hours (Mw) |
|---|---|
| Sample 11 | 9559 |

<Discussion>

From Table 8, it is understood that for the peptide composition of sample 11, the molecular weight of the collagen raw material was reduced by passing through the second step.

[Eighth Test]

<Weight Average Molecular Weight of Collagen Peptide>

For sample 12, the degree to which the molecular weight of the collagen raw material had been reduced to form the collagen peptide by passing through the second step was examined. Specifically, for sample 12, the weight average molecular weight of the collagen peptide contained in the peptide composition after fermentation for 6 hours in the second step was determined by the above-described measurement method. Table 9 shows the results.

TABLE 9

| | Weight average molecular weight after fermentation for 6 hours (Mw) |
|---|---|
| Sample 12 | 1200 |

<Discussion>

From Table 9, it is understood that for the peptide composition of sample 12, the molecular weight of the collagen raw material was reduced by passing through the second step.

[Ninth Test]

<Sensory Taste Test>

Samples 1 to 6 and samples 101 to 103 were each adjusted to a collagen peptide concentration of 10 mass % using RO water, and provided in an amount of 20 mL. Further, for sample 10, a solution (20 mL) obtained by dissolving 2 g of the dry powder in 18 mL of RO water was provided. For the samples, five evaluators conducted a sensory taste test on how strongly the taste peculiar to collagen was sensed. In the sensory taste test, scores 1 to 4 were given to the samples as shown in Table 10. As the score increases, the taste peculiar to collagen is evaluated to be reduced. Table 11 shows the results.

TABLE 10

| Score | Evaluation |
|---|---|
| 1 | Very strong taste peculiar to collagen is sensed |
| 2 | Strong taste peculiar to collagen is sensed |
| 3 | Taste peculiar to collagen is sensed |
| 4 | Little taste peculiar to collagen is sensed |

TABLE 11

| | Evaluator A | Evaluator B | Evaluator C | Evaluator D | Evaluator E | Average value |
|---|---|---|---|---|---|---|
| Sample 1 | 2 | 4 | 4 | 4 | 4 | 3.6 |
| Sample 2 | 3 | 4 | 4 | 3 | 3 | 3.4 |
| Sample 3 | 3 | 3 | 3 | 3 | 4 | 3.2 |
| Sample 4 | 3 | 4 | 4 | 4 | 4 | 3.8 |
| Sample 5 | 3 | 4 | 4 | 3 | 2 | 3.2 |
| Sample 6 | 2 | 3 | 3 | 3 | 2 | 2.6 |
| Sample 10 | 4 | 4 | 4 | 3 | 3 | 3.6 |
| Sample 101 | 2 | 3 | 2 | 1 | 2 | 2 |
| Sample 102 | 1 | 1 | 1 | 1 | 1 | 1 |
| Sample 103 | 1 | 2 | 1 | 2 | 1 | 1.4 |

<Discussion>

From Table 2, it was evaluated that the peptide compositions of samples 1 to 6 and 10 have a reduced taste peculiar to collagen as compared to the peptide compositions of samples 101 to 103.

CONCLUSION

From the above, it is indicated that the peptide compositions of samples 1 to 12 comprise a collagen peptide having a reduced molecular weight and have a reduced collagen smell and taste peculiar to collagen. In particular, the results for samples 4, 5 and 10 in the second test indicate that the peptide compositions of samples 1 to 12 have a reduced collagen smell and taste peculiar to collagen because these peptide compositions contain at least three first compounds. Accordingly, the peptide compositions of samples 1 to 12 may be particularly suitable for food applications or cosmetic product applications.

The embodiments and Examples disclosed herein are illustrative in every respect, and should not be construed as being limiting. The scope of the present invention is given not by the above description but by claims, and is intended to include all changes within the meaning and limit equivalent to those of claims.

The invention claimed is:

1. A peptide composition, comprising a collagen peptide, and isovaleric aldehyde, 1-octen-3-ol, phenylacetaldehyde and methional, wherein the peptide composition comprises the isovaleric aldehyde, 1-octen-3-ol, phenylacetaldehyde and methional at 0.05 ppm or more as a total amount thereof, and the peptide composition comprises the methional at 0.04 ppm or more.

2. The peptide composition according to claim 1, wherein the peptide composition comprises the at least three compounds at 0.4 ppm or more.

3. The peptide composition according to claim 1, wherein the collagen peptide has a weight average molecular weight of 20000 or less.

4. The peptide composition according to claim 1, wherein the peptide composition is a food or a cosmetic product.

* * * * *